United States Patent [19]

Pragnell et al.

[11] Patent Number: 5,674,841
[45] Date of Patent: Oct. 7, 1997

[54] METHOD FOR INHIBITING GROWTH OF STEM CELLS

[75] Inventors: Ian B. Pragnell, Glasgow, Scotland; Debra D. Donaldson, Cambridge, Mass.; Gerald J. Graham, Glasgow, Scotland; Gordon G. Wong, Jamaica Plain, Mass.

[73] Assignee: Genetics Institute, Inc., Cambridge, Mass.

[21] Appl. No.: 230,574

[22] Filed: Apr. 21, 1994

Related U.S. Application Data

[60] Continuation of Ser. No. 920,934, Jul. 28, 1992, abandoned, which is a division of Ser. No. 581,713, Sep. 13, 1990, abandoned, which is a continuation-in-part of Ser. No. 412,303, Sep. 25, 1989, abandoned.

[51] Int. Cl.$^6$ .................. A61K 38/17; C07K 14/435; C07K 14/47
[52] U.S. Cl. .................. 514/12; 514/2; 530/300; 530/324
[58] Field of Search .................. 424/85.1; 514/12; 530/350, 351, 300, 324; 512/2

[56] References Cited

U.S. PATENT DOCUMENTS

| | | | |
|---|---|---|---|
| 4,822,776 | 4/1989 | Cerami et al. | 514/21 |
| 5,278,145 | 1/1994 | Keller | 514/12 |

FOREIGN PATENT DOCUMENTS

| | | |
|---|---|---|
| 0310316 | 4/1989 | European Pat. Off. |
| WO9002762 | 3/1990 | WIPO |

OTHER PUBLICATIONS

Graham, G.J. et al. *Nature* 344:442–444 (1990).
Ignat'eva, O. et al *Biull. Eksp. Biol Med.* 98(9):326–9 (1984).
Wright, E.G. et al. *Leukemia Research* 4(6):537–545 (1989).
Obaru, K. et al. *J. Biochem.* 99:885–894 (1986).
I. B. Pragnell et al. Chem. Abstr., 109:344, abstract 89048m (1988).
E. G. Wright et al, Experimental Hematology, 16(6):473 (1988).
A. Janowska-Wieczorek et al, Proc. Am. Assoc. Cancer Res. Annu. Meet., 28(0):409 (1987).
M. Guigon et al, Chem. Abstracts, 96:36, abstract 115633h (1982).
M. Guigon et al, Cancer Res., 42:638–641 (1982).
H. E. Broxmeyer et al, J. Exp. Med., 170:1583–1594 (1989).
G. Davatelis et al, Science, 24:1066–1068 (1989).
T. J. Fahey III et al, Surg. Forum, 40:73–75 (1989) [Fahey I].
J. Minano et al, Abstract 2634, FASEB J., 4(3):A721 (1990).
T. J. Fahey III et al, Abstract 2078, FASEB J., 4(3):A624 (1990).
B. I. Lord et al, "Potential Therapeutic Value of Endogenous Stem Cell Proliferation Regulators", in Maturation Factors and Cancer, ed. Malcolm A.S. More (New York 1982), pp. 323–333.
K. Saukkonon et al, J. Exp. Med., 171:439–448 (1990).
S. Wolpe and A. Cerami, FASEB J., 3:2565–2573 (1989).
S. Wolpe et al, Abstract H141, J. Cell Biochem. Suppl., 0(13 Part C):21 (1989).
S. Wolpe et al, J. Exp. Med., 167:570–581 (1988).
M. Nakao et al, Mol. and Cell Biol., 10(7):3646–3658 (1990).
P. Zipfel et al, J. Immun., 142(5):1582–1590 (1989).
K. Obaru et al, J. Biochem., 99:885–894 (1986).
M. Miller et al, J. Immunol., 143:2907–2916 (1989).
K. Brown et al, J. Immunol., 142:679–687 (1989).
B. I. Lord et al, Brit. J. Haematology, 34:441–445 (1976).
E. G. Wright et al, Leukemia Research, 4(6):537–545 (1980).
T. M. Dexter and H. White, Nature, 344:380–381 (1990).
E. G. Wright et al, Cell Tissue Kinet., 18:193–199 (1985).
M. A. Lipes et al, Proc. Natl. Acad. Sci. USA, 85:9704–9708 (1988).
I. B. Pragnell et al, Blood, 72(1):196–201 (1988).
G. J. Graham et al, Nature, 334:442 (1990).

*Primary Examiner*—Dian C. Jacobson
*Attorney, Agent, or Firm*—Scott A. Brown; Thomas J. DesRosier

[57] ABSTRACT

The present invention discloses a method for protecting cycling or dividing stem cells from the cytotoxic effects of chemotherapeutic agents and radiation by administering prior to exposure to these agents, an effective amount of Stem Cell Inhibitory Factor as well as a composition useful therefore.

9 Claims, No Drawings

5,674,841

METHOD FOR INHIBITING GROWTH OF STEM CELLS

CROSS-REFERENCE TO RELATED APPLICATION

This application is a continuation of application Ser. No. 07/920,934, filed Jul. 28, 1992, now abandoned, which was a division of application Ser. No. 07/581,713, filed Sep. 13, 1990, now abandoned, which was a continuation-in-part of U.S. patent application, Ser. No. 07/412,303, filed Sep. 25, 1989, now abandoned.

The present invention relates generally to the treatment of human or animal subjects anticipating exposure to chemotherapeutic agents, radiation exposure, or other agents which irreparably damage cycling stem cells and a stem cell inhibitory composition useful therefore.

BACKGROUND OF THE INVENTION

In the treatment of subjects with cancer, conventional chemotherapy involves the application of one or more cell cycle specific cytotoxic agents, which have the adverse effect of killing, or irreparably damaging, both normal and cancer cells undergoing division. The goal of such chemotherapeutic agents, e.g., cytosine arabinoside (ara-C), is to destroy or disable the dividing cancer cells, preventing further cancer cell growth. A presently unavoidable effect of chemotherapy, however, is the destruction of other normal dividing cells, particularly the stem cells of the hematopoietic system and the epithelial stem cells which line the scalp and gut. Stem cell damage caused by the administration of chemotherapy, result in the usual side effects thereof, such as hair loss, stomach and intestinal damage, skin damage, myelosuppression, anemia, reduced immune function or response and the resulting increased sensitivity to infection.

A characteristic property of stem cells is their quiescent nature within the cell cycle. When there is 'insult' to the bone marrow, such as by drug treatment, radiation, severe blood loss, inflammatory reaction, or infection, the stem cell responds by a feedback mechanism to begin cycling to replenish the more mature progenitor cells, which in turn, differentiate into the required mature cells of the hematopoietic, immune or epithelial systems.

Since the hematopoietic stem cells are necessary for the development of all of the mature cells of the hematopoietic and immune systems, their survival is essential in order to reestablish in the subject treated with chemotherapy, a fully functional host defense system. Similarly, survival of epithelial stem cells is necessary for repair of the epithelial linings of organs, including the skin. Because high doses of cycle specific chemotherapeutic drugs, such as ara-C, effectively kill hematopoietic stem cells and stem cells of epithelial tissues, patients exposed to such agents suffer from serious side effects and are frequently at risk of serious infections.

Similar destruction of stem cells occurs upon exposure to a variety of dosages of radiation, whether the radiation is used for therapeutic purposes or is the result of accidental or unavoidable exposure to radiation, e.g., incident to a clean-up of, or presence at the location of, a nuclear accident at a power plant, or on a nuclear submarine. Subjects exposed to radiation also experience the destruction of their hematopoietic stem cells, and consequent failure or serious damage to the hematopoietic and immune systems. Radiation also kills dividing epithelial cells with consequent damage to many epithelial tissues.

While agents, such as the colony stimulating factors, e.g., M-CSF, CSF-1, GM-CSF, and others, are presently being employed to stimulate the development of certain hematopoietic cell lineages in subjects exposed to chemotherapy or radiation, such agents are not believed to be capable of restoring the hematopoietic system if an insufficient quantity of stem cells is present in the subject after such exposure.

Thus, there remains a need in the art for other therapeutic agents capable of protecting stem cells from the damaging effects of chemotherapy or radiation.

SUMMARY OF THE INVENTION

The present invention addresses this need in the art by providing a method of treating a subject anticipating exposure to an agent capable of killing dividing or cycling stem cells by administering to that subject an effective amount of a stem cell inhibitory composition. The stem cells protected by this method may be hematopoietic stem cells ordinarily present and dividing in the bone marrow. Alternatively, stem cells may be epithelial, located e.g., in the intestines or scalp or other areas of the body. The method of this invention may be desirably employed on humans, although animal treatment is also encompassed by this method.

The stem cell inhibitory composition useful in this method comprises an effective amount of a polypeptide or fragment of a protein referred to herein as Stem Cell Inhibitor Factor (SCIF) and described with specificity below.

In another aspect, the invention provides a method for protecting and restoring the hematopoietic, myeloid and immune systems of a patient undergoing chemotherapy, which includes administering to the patient an effective amount of SCIF. SCIF may be administered prior to the chemotherapy. Alternatively the SCIF may be administered during chemotherapy. Another alternative is administering the SCIF for a period after the chemotherapeutic regimen. Following chemotherapy, the patient may be treated with therapeutic factors, such as colony stimulating factors or other lymphokines that stimulate the stem cells to divide and further stimulate the production of more mature cells of the hematopoietic lineages.

In still a further aspect, the present invention involves a method for adjunctively treating any cancer, including those characterized by solid tumors, by administering to a patient having cancer an effective amount of SCIF to protect the hematopoietic stem cells of the bone marrow, thereby allowing greater dosages of chemotherapeutics or radiation to be employed for treatment of the cancer.

Yet another aspect of the present invention involves the treatment of leukemia comprising treating bone marrow cells having proliferating leukemia cells therein with an effective amount of SCIF to inhibit proliferation of normal stem cells, and treating the bone marrow with a cytotoxic agent to destroy leukemia cells. This method may be enhanced by the follow-up treatment of the bone marrow with other agents that stimulate its proliferation, e.g., lymphokines. This method may be performed in vivo. Alternatively, this method may be performed ex vivo and the resulting marrow purged of leukemia cells by the chemotherapeutic agent. The marrow may then be reinjected into the patient.

In still a further aspect, the method involves treating a subject having any disorder caused by proliferating stem cells. Such a disorder, such as psoriasis, may be treated by administering to the subject an effective amount of SCIF to partially or wholly inhibit proliferation of the stem cell in question.

Other aspects and advantages of the present invention will be apparent upon consideration of the following detailed description of preferred embodiments thereof.

DETAILED DESCRIPTION OF THE INVENTION

The present invention provides a method for reversibly protecting stem cells from damage from a cytotoxic agent capable of killing dividing stem cells. The method involves administering to a subject anticipating exposure to such an agent an effective amount of a Stem Cell Inhibitory Factor (SCIF). The method also may involve extending the SCIF treatment throughout the cytotoxic treatment to enhance the stem cell protective effect.

SCIF can reversibly inhibit division of a variety of stem cells in the human body. Specifically SCIF is effective in temporarily inhibiting cell division of hematopoietic stem cells. Additionally, SCIF also acts to inhibit cycling or dividing epithelial stem cells, located throughout the body. Other stem cell populations on which SCIF may exercise a reversibly inhibiting activity include male and female germinal cells; SCIF may then be employed to protect a male or female patient from post-chemotherapeutic germinal aplasia. Additionally, because chemotherapeutic agents commonly induce alopecia and mucositis, SCIF may be used to reversibly protect hair follicles and orogastrointestinal epithelial stem cells from adverse side effects of chemotherapy or radiation.

Thus the method of this invention may be employed in alleviating the undesirable side effects of chemotherapy on the patient's hematopoietic, myeloid and immune systems by protecting stem cells from damage from a chemotherapeutic agent, such as a cytotoxic drug or radiation dosage normally used to destroy cancer cells. Such an application of SCIF may also serve to protect epithelial stem cells during chemotherapy. SCIF may be administered to the patient in a dosage sufficient to inhibit stem cell division for a time sufficient to allow the action of the chemotherapeutic agent. After the chemotherapeutic agent has performed its function, the stem cells inhibited by SCIF will without further treatment, revert to dividing cells. If it is desired to enhance the reversion of hematopoietic stem cells, the patient can receive doses of hematopoietic growth factors or cytokines used to stimulate the growth and development of hematopoietic cells.

The majority of chemotherapeutic agents used for cancer chemotherapy have a relatively short in vivo half-life, usually less than 24 hours. This inhibitory effect of SCIF according to the present invention is maintained for at least the major proportion of the effective time during which the chemotherapeutic agent is active in vivo. For those cytotoxic agents which have prolonged half-lives (e.g., greater than 24 hours), it is expected that more prolonged treatment with SCIF would be required. The normal physiological mechanisms within the subject would limit the effective duration of activity of SCIF in relation to cycling stem cells.

Additionally, the method has utility in providing a subject protection against other exposure to radiation, which damages the bone marrow cells of a subject. An individual may be administered SCIF where unintentional or accidental exposure to dangerous levels of radiation are anticipated. For example, such individuals anticipating entering sites of nuclear fall-out, persons responsible for examining and cleaning nuclear power plants after a leak of dangerous levels of radiation or nuclear submarines and the like may be treated by this method to inhibit replicating stem cell division in case of short term radiation exposure. SCIF administration during, as well as before radiation exposure may provide enhanced protection. Additionally, SCIF may be employed in this method as an adjunctive treatment with chemotherapy to treat any cancers. Because the bone marrow is the limiting organ in determining the amount of radiation or dosage of cytotoxic drug that can be applied to a patient, SCIF may be used to protect the bone marrow hematopoietic cells from radiation or chemotherapy, thereby allowing greater amounts of radiation or drugs to be applied to treat any cancer, normally amenable to either radiation or chemotherapeutic treatment. Since the myelotoxicity of the cytotoxic drugs is also limiting on their dosage during chemotherapy, the administration of SCIF to the patient is likely to enable increased drug dosages to be given to the patient without the serious side effects that would normally accompany such increased dosages.

The method may also be employed to treat solid tumors by inhibiting during chemotherapeutic treatment, the division of epithelial stem cells.

SCIF may also be employed in a method for preparing autologous bone marrow for transplantation. The marrow can be treated ex vivo with an effective amount of SCIF to inhibit stem cell division and then purged of cancerous cells by administering an effective amount of a chemotherapeutic agent or radiation. Marrow thus treated may be reinjected into the autologous donor. Optionally the patient may then be treated with an agent known to stimulate hematopoiesis.

SCIF may also be employed in the method of this invention as an adjunctive therapy in the treatment of leukemia. For example, where the leukemic cells do not respond to SCIF, the leukemic bone marrow cells may be treated ex vivo, with SCIF. The proliferation of normal stem cells is prevented by administration of SCIF. Thus, during the time that the proliferating leukemic cells are treated with a cytotoxic agent, a quantity of normal stem cells are protected from damage. Additionally, a stimulatory cytokine, such as IL-3 or GM-CSF, may be administered to induce cycling in the leukemic cells during drug or radiation treatment while the normal stem cells are protected with SCIF.

For ex vivo use, the bone marrow may be treated with SCIF to inhibit stem cell division, thereby protecting stem cells from destruction by the subsequent application to the marrow or to the source of any other cancer, of chemotherapy designed to destroy cycling cells, e.g. leukemic cells. The resulting purged marrow may be reinjected into the patient, wherein the stem cells will begin to divide normally. To enhance cell division of the hematopoietic stem cells, the lymphokines and cytokines above-identified may also be administered. The same process may be accomplished by administering SCIF to the patient in vivo.

The method of this invention may also be employed to treat disorders related to hyperproliferative stem cells. For example, psoriasis is a disorder caused by hyperproliferating epithelial cells of the skin and is sometimes treated with cytotoxic drugs. Similarly, a condition of in situ dysplasia of cervical epithelium is recognized which will proceed to cervical cancer if left untreated. Both of these transitional states may be treated prophylactically with SCIF. Other pre-neoplastic lesions in which stem cell proliferation is involved may also be amenable to effective amounts of SCIF employed to inhibit wholly or partially the proliferation of the stem cells. For these uses, topical or transdermal compositions containing SCIF may be employed, as well as other parenteral means of administering SCIF.

The SCIF polypeptides may also be used in another method of this invention. Antibodies, monoclonal or polyclonal, may be developed by standard techniques to the SCIF polypeptides. These antibodies or SCIF polypeptides may be labelled with detectable labels of which many types are known in the art. The labeled SCIF or anti-SCIF antibodies may then be employed as stem cell markers to identify and isolate stem cells by administering to a patient directly for diagnostic purposes. Alternatively these labeled polypeptides or antibodies may be employed ex vivo to identify stem cells in a bone marrow preparation, to enable their removal prior to purging techniques. In the same manner such labeled polypeptides or antibodies may be employed to isolate and identify epithelial, or other stem cells.

The inventors herein have discovered that SCIF, employed in the following methods and examples, is the murine homologue of protein factors previously identified. K. Obaru et al, *J. Biochem.*, 99:885–894 (1986) identified the amino acid and DNA sequence of a gene found to be inducible by tumor promoters such as phorbol ester in human tonsillar lymphocytes. The authors predicted that this gene produced a protein which may signal proliferation of T cells. More recently, P. F. Zipfel et al, *J. Immunol.*, 142:1582–1590 (1989) reported that the same protein was produced by mitogenic activation of human T cells and suggested that it may function as a lymphokine or cytokine.

The present method thus desirably employs the human SCIF factor in human therapy. This SCIF factor may be the human polypeptide encoded by these prior art sequences. The Obaru/Zipfel SCIF sequence is reported below in Table I. Alternatively, this factor may be obtained as described in Example 1 below. The human analog of SCIF was obtained from a human T cell line using oligonucleotides based on the published LD 78 sequence of Obaru et al, cited above. Human SCIF demonstrates human activity identical to the murine protein in the SCIF assays described below.

The human SCIF clone of Example 1 has been substantially sequenced. While exhibiting the required activity, this sequence has been found to differ in both nucleotide and amino acid sequence from the published sequence. The alternative human SCIF DNA and amino acid sequence of Example 1 is reported below in Table II. The sequence within the brackets has not yet been determined. The sequence that does appear within the brackets on Table II has been derived from the published LD 78 sequence of Obaru et al and may or may not be identical with the human SCIF clone. The differences in the nucleotide sequence between the cloned SCIF sequence of Example 1 and the published Obaru sequence are indicated in Table II by asterisks above the changed or added amino acids and below the changed nucleotides. Dashes indicate non-coding sequences not found in the sequence of Example 1. There are 18 nucleotide differences and 4 amino acid differences between the two SCIF sequences. Additionally the human clone includes 3 more nucleotides and an additional amino acid in contrast to the published sequence.

However, also useful in the present invention as a SCIF molecule are other proteins encoded by other DNA sequences, not identical to that of the prior art references. Such DNA sequences are characterized as capable of hybridizing under stringent hybridization conditions [see, T. Maniatis et al, *Molecular Cloning* (A Laboratory Manual), Cold Spring Harbor Laboratory (1982), pages 387 to 389] to the human SCIF (or Obaru et al) DNA sequences and coding on expression for polypeptides or proteins capable of demonstrating SCIF activity as described herein. An example of one such stringent hybridization condition is hybridization at 4XSSC at 65° C., followed by a washing in 0.1XSSC at 65° C. for an hour. Alternatively an exemplary stringent hybridization condition is in 50% formamide, 4XSSC at 42° C.

Other human SCIF proteins or polypeptides may be encoded by other DNA sequences which hybridize to the sequences for human SCIF (Obaru et al sequence and the sequence obtained from the clone of Example 1) under relaxed hybridization conditions and which code on expression for peptides having SCIF biological properties. Examples of such non-stringent hybridization conditions are 4XSSC at 50° C. or hybridization with 30–40% formamide at 42° C. For example, the molecule identified previously as human MIP-beta, may be useful in the method of this invention, if capable of displaying stem cell inhibitory activity as defined hereinbelow by assay.

In a like manner other SCIF polypeptides may be characterized by amino acid sequences which differ from the Obaru et al sequence or the sequence obtained from the clone of Example 1 due to allelic variations (naturally-occurring base changes in the species population which may or may not result in an amino acid change). SCIF polypeptides encoded by DNA sequences which differ in codon sequence due to the degeneracies of the genetic code or allelic variations are also expected to be useful in the method of this invention. Variations in the DNA sequence of SCIF which are caused by point mutations or by induced modifications to enhance the activity, half-life or production of the polypeptides encoded thereby are also encompassed in the invention and expected to be useful in the disclosed method.

The method of the present invention may also employ the murine factor (also known as macrophage inflammatory protein I-alpha, MIP-1 alpha). Murine MIP-1 beta does not have stem cell inhibitory activity. The sequence of the molecule here identified as murine SCIF is reported in Davatelis et al, *J. Exp. Med.*, 167:1939–1944 (1988) incorporated herein by reference. The stem cell inhibitory function of this molecule was not recognized in that reference. The murine factor may also be employed in the methods of this invention, provided that it provokes no antibody generation from the human immune system.

Obviously other species analogs of SCIF may be employed in various veterinary uses of the above identified methods.

TABLE I

AAGGACACGG GCAGCAGACA GTGGTCATGC CTTTCTTGGC TCTGCTGACA CTCGAGCCCA

|  |  |  |  |  |  |  |  | 1 |  |  |  |  |  | 10 |
|---|---|---|---|---|---|---|---|---|---|---|---|---|---|---|
|  |  |  |  |  |  |  |  | Met | Gln | Val | Ser | Thr | Ala | Ala | Leu | Ala | Val |

CATTCCGTCA CCTGCTCAGA ATC ATG CAG GTC TCC ACT GCT GCC CTT GCT GTC

|  |  |  |  |  | 20 |  |  |  |  |  |  |  |
|---|---|---|---|---|---|---|---|---|---|---|---|---|
| Leu | Leu | Cys | Thr | Met | Ala | Leu | Cys | Asn | Gln | Phe | Ser | Ala | Ser | Leu | Ala | Ala |

CTC CTC TGC ACC ATG GCT CTC TGC AAC CAG TTC TCT GCA TCA CTT GCT GCT

TABLE I-continued

```
                    30                                              40
Asp Thr Pro Thr Ala Cys Cys Phe Ser Tyr Thr Ser Arg Gln Ile Pro Gln
GAC ACG CCG ACC GCC TGC TGC TTC AGC TAC ACC TCC CGG CAG ATT CCA CAG 50                                          60
Asn Phe Ile Ala Asp Tyr Phe Glu Thr Ser Ser Gln Cys Ser Lys Pro Gly
AAT TTC ATA GCT GAC TAC TTT GAG ACG AGC AGC CAG TGC TCC AAG CCG GGT

70
Val Ile Phe Leu Thr Lys Arg Ser Arg Gln Val Cys Ala Asp Pro Ser Glu
GTC ATC TTC CTA ACC AAG CGA AGC CGG CAG GTC TGT GCT GAC CCC AGT GAG 80                                  90
Glu Trp Val Gln Lys Tyr Val Ser Asp Leu Glu Leu Ser Ala Stop
GAG TGG GTC CAG AAA TAT GTC AGC GAC CTA GAG CTG AGT GCC TGA
```

GGGGTCCAGA AGCTTCGAGG CCCAGCGACC TCGGTGGGCC AGTGGGGAGG AGCAGGAGCC

TGAGCCTTGG GAAACATGCG TGTGACCTCC ACAGCTACCT CTTCTATGGA CTGGTTGTTG

CCAAACAGCC ACACTGRGGG ACTCTTCTTA ACTTAAATTT TAATTTATTT ATTTATACTA

TTTAGTTTTT GTAATTTATT TTCGATTTCA CAGTGTGTTT GTGATTGTTT GCTCTGAGAG

TTCCCCTGTC CCCTCCCCCT TCCCTCACAC CGCGTCTGGT GACAACCGAG TGGCTGTCAT

CAGCCTGTGT AGGCAGTCAT GGCACCAAAG CCACCAGACT GACAAATGTG TATCGGATGC

TTTTGTTCAG GGCTGTGATC GGCCTGGGGA AATAATAAAG ACGCTCTTTT AAAAGGTAAA

AAAAAAAAAA AAAAAA

TABLE II

```
                                                    1
                    *                **             Met Gln Val Ser Thr Ala
- - - CTCGAGCCCA CATTCCATCA CCTGCTCCCA ATC ATG CAG GTC TCC ACT GCT 10                                      20  *   *
Ala Leu Ala Val Leu Leu Cys Thr Met Ala Leu Cys Asn Gln Val Leu Ser
GCC CTT GCC GTC CTC CTC TGC ACC ATG GCT CTC TGC AAC CAG GTC CTC TCT
                                                    *       ***

*               30                                         40
Ala Pro Leu Ala Ala Asp Thr Pro Thr Ala Cys Cys Phe Ser Tyr Thr Ser
GCA CCA CTT GCT GCT GAC ACG CCG ACC GCC TGC TGC TTC AGC TAC ACC TCC
    *

50
Arg Gln Ile Pro Gln Asn Phe Ile Ala Asp Tyr Phe Glu Thr Ser Ser Gln
CGA CAG ATT CCA CAG AAT TTC ATA GCT GAC TAC TTT GAG ACG AGC AGC CAG
 *

60          *                           70*
Cys Ser Lys Pro Ser Val Ile Phe Leu Thr Lys Arg Gly Arg Gln Val Cys
TGC TCC AAG CCC AGT GTC ATC TTC CTA ACC AAG AGA GGC CGG CAG GTC TGT
                *                           *   *

80                                      90
Ala Asp Pro Ser Glu Glu Trp Val Gln Lys Tyr Val Ser Asp Leu Glu Leu
GCT GAC CCC AGT GAG GAG TGG GTC CAG AAA TAC GTC AGT GAC CTG GAG CTG
                                            *       *   *   *

Ser Ala Stop
AGT GCC TGA [GGGGTCCAGA AGCTTCGAGG CCCAGCGACC TCGGTGGGCC AGTGGGGAGG
```

AGCAGGAGCC TGAGCCTTGG GAAACATGCG TGTGACCTCC ACAGCTACCT CTTCTATGGA

CTGGTTGTTG CCAAACAGCC ACACTGRGGG ACTCTTCTTA ACTTAAATTT TAATTTATTT

ATTTATACTA TTTAGTTTTT GTAATTTATT TTCGATTTCA CAGTGTGTTT GTGATTGTTT

GCTCTGAGAG TTCCCCTGTC CCCTCCCCCT TCCCTCACAC CGCGTCTGGT GACAACC]GA

GTGGCTGTCA TCGGCCTGTG TAGGCAGTCA TGGCACCAAA GCCACCAGAC TGACAAATGT
            *

TABLE II-continued

```
GTATCAGATG CTTTTGTTCA GGGCTGTGAT CGGCCTGGGG AAATAATAAA GATGTTCTTT
    *                                                    *  *

TAAACGGTAA AAA------  --------
    *
```

This stem cell inhibitory function of LD78 or murine MIP-1 alpha identified in the references described above, has heretofore never been identified as a function of this protein despite the extensive work of researchers on this factor. See, e.g., Obaru et al and Zipfel et al, cited above.

The stem cell inhibitory factor acts on cycling stem cells by reversibly placing them in an undividing "resting" state. When the stem cells are initially treated in this way, the subsequent application of chemotherapy or radiation does not kill the stem cells because the cells are not dividing. Thus, after exposure to the chemotherapy or radiation, the stem cells may be "reactivated" to generate dividing progenitor cells, by discontinuing the administration of SCIF.

An additional means of stimulating the resting stem cells into division may also be the administration to the subject of other colony stimulating factors, e.g., M-CSF, CSF-1, GM-CSF, G-CSF, Meg-CSF or other cytokines, such as IL-1, IL-2, IL-3, IL-4, IL-5, IL-6, IL-7, IL-9, IL-11 and erythropoietin following the chemotherapy or radiation exposure.

SCIF polypeptides or active fragments having stem cell inhibitory activity, may be produced by known conventional chemical synthesis or recombinant techniques employing the amino acid and DNA sequences of Table I or Table II, above. For example, SCIF polypeptides may be produced by culturing a suitable cell or cell line, which has been transformed with a DNA sequence coding on expression for a SCIF polypeptide or active fragment thereof under the control of known regulatory sequences. The resulting protein may be isolated from the cells, cell lysate, or medium by conventional techniques. Suitable techniques for such production of recombinant SCIF are described in, e.g., T. Maniatis et al, Molecular Cloning-A Laboratory Manual, Cold Spring Harbor Laboratory, Cold Spring Harbor, N.Y. (1982).

Methods for constructing SCIF polypeptides useful in the method of the present invention by chemical synthetic means are also known to those of skill in the art. See, e.g., Merrifield in J.A.C.S, 85: 2149–2154 (1963) or Peptide Synthesis" by Bodanszky, et al, second edition, John Wiley and Sons, 1976.

The recombinant or synthetically-constructed SCIF polypeptide sequences, by virtue of sharing primary, secondary, or tertiary structural and conformational characteristics with SCIF polypeptides may possess the same biological characteristic of inhibiting stem cell division in common with the human factor identified above in Table I or Table II.

Modifications in the peptides or DNA sequences encoding SCIF or active fragments thereof may also be made and are believed to be useful also in the method of this invention, where the modified SCIF peptide or fragment thereof shares the desired stem cell inhibitory biological activity. Modifications of interest in the SCIF sequences may include the replacement, insertion or deletion of a selected amino acid residue in the coding sequences. Mutagenic techniques for such replacement, insertion or deletion are well known to one skilled in the art. [See, e.g., U.S. Pat. No. 4,518,584.]

Specific mutations of the sequences of the SCIF polypeptide may involve the insertion of an asparagine-linked glycosylation site, either Asp-X-Thr or Asp-X-Ser, where X can be any amino acid, into the sequence or a sequence modification at any site of the molecule that is modified by addition of O-linked carbohydrate.

Other analogs and derivatives of the sequence of SCIF which would be expected to retain SCIF activity in whole or in part may also be easily made by one of skill in the art and may be useful in the methods of this invention.

Recombinant production of SCIF is presently preferred. The human cDNA may be isolated and inserted into suitable cells or cell lines under the control of appropriate regulatory sequences. Suitable host cells for production of the protein may be mammalian cells, such as Chinese hamster ovary cells (CHO) or 3T3 cells. The selection of suitable mammalian host cells and methods for transformation, culture, amplification, screening and product production and purification are known in the art. See, e.g., Gething and Sambrook, Nature, 293:620–625 (1981), or alternatively, Kaufman et al, Mol. Cell. Biol., 5(7):1750–1759 (1985) or Howley et al, U.S. Pat. No. 4,419,446. Other suitable mammalian cell lines are the monkey COS-1 cell line, and the CV-1 cell line.

Similarly useful as host cells suitable for the production of SCIF for use in the present invention are bacterial cells. For example, the various strains of E. coli (e.g., HB101, MC1061 and strains used in the following examples) are well-known as host cells in the field of biotechnology. Various strains of B. subtilis, Pseudomonas, other bacilli and the like may also be employed in this method.

Many strains of yeast cells known to those skilled in the art are also available as host cells for expression of the polypeptides of the present invention. Additionally, where desired, insect cells may be utilized as host cells in the method of the present invention. See, e.g., Miller et al, Genetic Engineering, 8:277–298 (Plenum Press 1986) and references cited therein.

It may also be possible to employ one or more peptide fragments of SCIF, which retain the stem cell inhibitory activity of intact SCIF molecule, for use in the present methods for protecting a subject's stem cells from destruction by exposure to an agent capable of killing dividing stem cells.

For use in the method for protecting stem cells according to this invention a therapeutically effective amount of the SCIF protein or a therapeutically effective fragment thereof may be employed in admixture with a pharmaceutically acceptable carrier. Where desirable, this SCIF composition can be systemically administered parenterally. In clinical applications, it may be desirable to target the SCIF to the blood-forming tissue, e.g., bone marrow. This targeting can be achieved by injecting the SCIF, normally by infusion or bolus intravenous administration. Alternatively, the SCIF can be targeted by varying the pharmaceutical formulation of the drug, e.g. by linking it to agents which have been shown to target to the bone marrow. This formulation can be administered intravenously. If desirable, the composition may be administered subcutaneously.

When systematically administered, the therapeutic composition for use in this invention is in the form of a pyrogen-free, parenterally acceptable aqueous solution. The preparation of such a pharmaceutically acceptable protein solution, having due regard to pH, isotonicity, stability and the like, is within the skill of the art. For administration in the method for treating hyperproliferating stem cells, the composition containing SCIF may be administered topically or through a transdermal patch to localize its effect on the area of hyperproliferation.

The dosage regimen involved in a method for treating the subject anticipating exposure to such cytotoxic agents or for treatment of hyperproliferating stem cells will be determined by the attending physician considering various factors which modify the action of drugs, e.g. the condition, body weight, sex and diet of the patient, the severity of any infection, time of administration and other clinical factors. Generally, the daily regimen should be in the range of 1–1000 micrograms of SCIF protein or fragment thereof per kilogram of body weight.

Following the subject's exposure to the cytotoxic agent or radiation, the therapeutic method of the present invention may also employ administering to the subject one or more lymphokines, colony stimulating factors or other cytokines, hematopoietins, interleukins, growth factors to generally stimulate the growth and division of the stem cells inhibited by the prior treatment with SCIF. Such therapeutic agents which encourage hematopoiesis include IL-1, IL-2, IL-3, IL-4, IL-5, IL-6, IL-7, Meg-CSF, M-CSF, CSF-1, GM-CSF, G-CSF or erythropoietin. The dosages of these agents may be employed in the same ranges as the dosages for SCIF recited above. In a like manner, these dosages would be adjusted to compensate for variations in the physical condition of the patient, and the amount and type of chemotherapeutic agent or radiation to which the subject was exposed. Progress of the reversal of the inhibition of the stem cells caused by administration of SCIF in the treated patient can be monitored by conventional methods.

In the treatment of leukemia, it may prove beneficial to administer both SCIF to inhibit normal stem cell cycling and a stimulator of leukemic cell growth, such as IL-3 or GM-CSF, simultaneously with the cytotoxic drug treatment or during radiation. By this protocol, it should be possible to achieve the greatest differences between the cycling statuses of normal and leukemic cells.

The following examples illustratively describe the use of murine SCIF in the in vitro stem cell assay. These examples are for illustration and do not limit the scope of the present invention.

EXAMPLE 1

Obtaining Human SCIF cDNA

Polyadenylated RNA isolated from the human T cell line C10-MJ2 was used as a template for synthesis of single stranded complementary DNA by standard procedures [see, e.g., Maniatis et al., cited above]. The presence of cDNAs encoding human SCIF were demonstrated by the polymerase chain reaction (PCR) employing stringent conditions [R. K. Saiki et al., Science, 230:1350 (1985)] using the following oligonucleotides based on the sequence of Table I:

5' AGCTCGAGAT CATGCAGGTC TCCACTG 3'
5' GCGAATTCCC TCAGGCACTC AGCTCCA 3'.

Double-stranded SCIF DNA obtained as the product of the PCR and labeled with (alpha $^{32}$P) dCTP by random priming was used to identify SCIF cDNAs in a previously constructed C10-MJ2 cDNA expression library [J. F. Moreau et al, Nature, 336:690 (1988)].

Conditioned media obtained from COS cells transfected with full-length SCIF cDNAs in the proper orientation were analyzed according to the assay described in Example 3. Sequencing of selected clones, named pXMT2.A1, pXMT2.A3 through pXMT2.A9, is ongoing.

The human SCIF sequence of Table II differs substantially from the Obaru et al LD 78 sequence of Table I, from which the oligonucleotides were derived. There are 18 base changes, 4 amino acid changes as well as three additional bases and an additional amino acid.

EXAMPLE 2

In Vitro Stem Cell Assay

For the detection of stem cells in vitro $10^4$ murine bone marrow cells from the murine macrophage cell line, J774.2 [P. Ralph et al, J. Immunol., 114:898–905 (1975)] in 4 ml supplemented alpha-modified minimal essential medium (MEM) containing 25% fetal calf or horse serum and 0.3% agar were seeded on top of an underlayer of the same medium containing 0.6% agar, 10% L929 cell conditioned medium (L929 CM, a source of the growth factor CSF-1) and 10% AF1-19T cell conditioned medium (AF1-19T CM) (a source of the growth factor GM-CSF and other uncharacterized stem cell growth factors) in a 6 cm petri dish. Cultures were incubated at 37° C. in a fully humidified atmosphere of 10% $CO_2$, 5% $O_2$, 85% $N_2$ for 11 days. Colonies can be stained with INT 2-(p-iodophenyl)-3-(p-nitrophenyl)-5-phenyl-tetrazolium chloride hydrate overnight.

While some colonies are present in the CFU-A assay having a diameter less than 2 mm, this value was selected as a useful cut-off point after preliminary experiments were performed using cytosine arabinoside. Within individual dishes, colonies with a diameter <2 mm were mainly derived from cells in cycle, whereas colonies >2 mm were found to be derived from minimally proliferating cells. Only colonies with diameters >2 mm were scored in these assays.

The assay, also described in I. B. Pragnell et al, Blood, 72:196–201 (1988), demonstrates that more mature progenitor cells are unaffected by treatment with SCIF, while cycling stem cells, after treatment with SCIF, become resistant to the action of cytosine arabinoside. If the treated stem cells are then washed with buffered saline to remove the cytotoxic drug and SCIF the surviving stem cells proliferate in culture normally as illustrated below.

EXAMPLE 3

Demonstration of the Effect of SCIF on CFU-A

Bone marrow cells were incubated in paired tubes containing $5\times10^6$ cells in 1 ml Fischer's medium supplemented with 20% horse serum. SCIF or alpha-MEM was added to each tube and Fischer's medium was added to control tubes. The mixtures were incubated at 37° C. for 5 hours (inhibition assays). For the last 60 minutes of the incubation $10^{-3}$M cytosine arabinoside was added to one tube and an equal volume of medium to the other tube. Cells were then washed twice before being assayed in the CFU-A assay as described above. SCIF was found to reduce the number of stem cells in cycle from an average of greater than 30% to an average of less than 10%. The untreated cells were killed by the cytotoxic drug treatment in contrast to the inhibitor treated stem cells.

Pure preparations of SCIF also reversibly trigger multipotential stem cells out of cycle when assayed in vivo using ara-C in the CFU-S assay described in Pragnell et al, cited above.

The purified and sequenced SCIF of this invention is a cytokine which has the ability to specifically reduce the proportion of haemopoietic stem cells in DNA synthesis, thereby protecting them from cytosine arabinoside, a cell-cycle specific cytotoxic drug. In contrast, SCIF does not affect the proliferation of more mature progenitors and so appears to be a specific regulator of the stem cell compartment. SCIF is active in the 200–500 pM range, as measured in the CFU-A direct addition assays.

EXAMPLE 4

Expression of Recombinant Human SCIF

To produce SCIF, the cDNA encoding it is transferred into an appropriate expression vector of which numerous types are known in the art for mammalian, insect, yeast, fungal and bacterial expression by standard molecular biology techniques. See, e.g., Y. C. Yang et al, *Cell*, 47:3–10 (1986). One such vector is the COS cell expression vector, pXM, containing the SV40 enhancer, major adenovirus late promoter, DHFR coding sequence, SV40 late message poly A addition site and VaI gene. This vector may be linearized with the endonuclease enzyme XhoI and ligated to equimolar amounts of SCIF cDNA which has been previously modified by the addition of synthetic oligonucleotides that generate complementary XhoI cohesive ends. Such oligonucleotides are commercially available [Collaborative Research, Lexington, Mass.]. The vector is then introduced into appropriate host cells by conventional genetic engineering techniques.

a. Mammalian Cell Expression

To obtain expression of SCIF polypeptide for use in the assays described below, the pXM vector containing the SCIF DNA sequence is transfected onto COS cells, for example. The conditioned medium for the transfected COS cells contains SCIF biological activity as measured in the assay described in Example 2.

The mammalian cell expression vectors described herein may be synthesized by techniques well known to those skilled in this art. The components of the vectors, e.g. replicons, selection genes, enhancers, promoters, and the like, may be obtained from natural sources or synthesized by known procedures. See, Kaufman et al, *J. Mol. Biol.*, 159:511–521 (1982); and Kaufman, *Proc. Natl. Acad. Sci., USA*, 82:689–693 (1985). Exemplary mammalian host cells include particularly primate cell lines and rodent cell lines, including transformed cell lines. Normal diploid cells, cell strains derived from in vitro culture of primary tissue, as well as primary explants, are also suitable. Candidate cells need not be genotypically deficient in the selection gene so long as the selection gene is dominantly acting. For stable integration of the vector DNA, and for subsequent amplification of the integrated vector DNA, both by conventional methods, CHO cells may be employed. Alternatively, the vector DNA may include all or part of the bovine papilloma virus genome [Lusky et al, *Cell*, 36:391–401 (1984)] and be carried in cell lines such as C127 mouse cells as a stable episomal element. Other suitable mammalian cell lines include but are not limited to, HeLa, COS-1 monkey cells, mouse L-929 cells, 3T3 lines derived from Swiss, Balb-c or NIH mice, BHK or HaK hamster cell lines.

Stable transformants are then screened for expression of the product by standard immunological or enzymatic assays. The presence of the DNA encoding the SCIF polypeptides may be detected by standard procedures such as Southern blotting. Transient expression of the DNA encoding the polypeptides during the several days after introduction of the expression vector DNA into suitable host cells, such as COS-1 monkey cells, is measured without selection by activity or immunologic assay of the proteins in the culture medium.

One skilled in the art can also construct other mammalian expression vectors comparable to the pXM/SCIF vector by, e.g., inserting the DNA sequence of SCIF from the respective plasmids with XhoI and employing well-known recombinant genetic engineering techniques and other known vectors, such as pJL3 and pJL4 [Gough et al., *EMBO J.*, 4:645–653 (1985)] and pMT2 (starting with pMT2-VWF, ATCC #67122; see PCT application PCT/US87/00033). The transformation of these vectors into appropriate host cells can result in expression of the SCIF polypeptides.

b. Bacterial Expression Systems

Similarly, one skilled in the art could manipulate the sequence of SCIF by eliminating any mammalian regulatory sequences flanking the coding sequences and inserting bacterial sequences to create bacterial vectors for intracellular or extracellular expression of the SCIF polypeptides of the invention by bacterial cells. The DNA encoding the factor may be further modified to contain different codons for bacterial expression as is known in the art. Preferably the sequence is operatively linked in-frame to a nucleotide sequence encoding a secretory leader polypeptide permitting bacterial expression, secretion and processing of the mature variant protein, also as is known in the art. The compounds expressed in bacterial host cells may then be recovered, purified, and/or characterized with respect to physiochemical, biochemical and/or clinical parameters, all by known methods.

c. Insect or Yeast Cell Expression

Similar manipulations can be performed for the construction of an insect vector [See, e.g., procedures described in published European patent application 155,476] for expression in insect cells. A yeast vector could also be constructed employing yeast regulatory sequences for intracellular or extracellular expression of the proteins of the present invention by yeast cells. [See, e.g., procedures described in published PCT application WO 86/00639 and European patent application EP 123,289.]

EXAMPLE 5

Construction of CHO Cell Lines Expressing High Levels of SCIF

One method for producing high levels of the SCIF polypeptides of the invention from mammalian cells involves the construction of cells containing multiple copies of the heterologous SCIF gene. The heterologous gene can be linked to an amplifiable marker, e.g., the dihydrofolate reductase (DHFR) gene for which cells containing increased gene copies can be selected for propagation in increasing concentrations of methotrexate (MTX) according to the procedures of Kaufman & Sharp, *J. Mol. Biol.*, (1982) supra. This approach can be employed with a number of different cell types.

For example, the pXM vector containing a SCIF gene in operative association with other plasmid sequences enabling expression thereof and the DHFR expression plasmid pAdD26SV(A)3 (Kaufman & Sharp, *Mol. Cell Biol.*, 3(9)

:1598–1608 (1983) can be co-introduced into DHFR-deficient CHO cells, DUKX-BII, by calcium phosphate coprecipitation and transfection. Alternatively, the SCIF gene may be introduced into pMT2 as previously mentioned and the resultant vector used in place of pXM/SCIF and pAdD26SV(A)3. DHFR expressing transformants are selected for growth in alpha media with dialyzed fetal calf serum, and subsequently selected for amplification by growth in increasing concentrations of MTX (sequential steps in 0.02, 0.2, 1.0 and 5uM MTX) as described in Kaufman et al., *Mol. Cell Biol.*, 5:1750 (1983). Transformants are cloned, and biologically active SCIF polypeptide expression is monitored by the assay of Example 2. SCIF polypeptide expression is expected to increase with increasing levels of MTX resistance.

Numerous modifications and variations in practice of this invention are expected to occur to those skilled in the art.

We claim:

1. A method for inhibiting growth of hematopoietic stem cells in a mammalian subject in need thereof comprising administering to said subject a stem cell inhibitory factor selected from the group consisting of a protein having the amino acid sequence set forth in Table I and a protein having the amino acid sequence set forth in Table II in an amount effective to inhibit growth of hematopoietic stem cells in said subject.

2. The method according to claim 1 wherein said stem cell inhibitory factor is a protein having the amino acid sequence set forth in Table I.

3. The method according to claim 1 wherein said stem cell inhibitory factor is a protein having the amino acid sequence set forth in Table II.

4. The method according to claim 1 wherein said subject is exposed to a cytotoxic agent capable of damaging dividing stem cells.

5. The method according to claim 4 wherein said agent is a chemotherapeutic agent capable of damaging stem cells undergoing division.

6. The method according to claim 4 wherein said agent is radiation sufficient to damage stem cells undergoing division.

7. The method according to claim 4 wherein said subject is exposed after administration of said factor.

8. The method according to claim 4 wherein said subject is exposed before administration of said factor.

9. The method according to claim 4 wherein said subject is exposed at the time of administration of said factor.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 800 base pairs
( B ) TYPE: nucleic acid
( C ) STRANDEDNESS: single
( D ) TOPOLOGY: linear ( i i ) MOLECULE TYPE: cDNA ( v i ) ORIGINAL SOURCE:
( A ) ORGANISM: Homo sapiens
( F ) TISSUE TYPE: Tonsillar
( G ) CELL TYPE: Lymphocyte
( H ) CELL LINE: LD78

( i x ) FEATURE:
( A ) NAME/KEY: CDS
( B ) LOCATION: 84..362

( x i ) SEQUENCE DESCRIPTION: SEQ ID NO:1:

```
AAGGACACGG GCAGCAGACA GTGGTCATGC CTTTCTTGGC TCTGCTGACA CTCGAGCCCA  60

CATTCCGTCA CCTGCTCAGA ATC ATG CAG GTC TCC ACT GCT GCC CTT GCT     110
                          Met Gln Val Ser Thr Ala Ala Leu Ala
                           1               5

GTC CTC CTC TGC ACC ATG GCT CTC TGC AAC CAG TTC TCT GCA TCA CTT   158
Val Leu Leu Cys Thr Met Ala Leu Cys Asn Gln Phe Ser Ala Ser Leu
 10                  15                  20                  25

GCT GCT GAC ACG CCG ACC GCC TGC TGC TTC AGC TAC ACC TCC CGG CAG   206
Ala Ala Asp Thr Pro Thr Ala Cys Cys Phe Ser Tyr Thr Ser Arg Gln
                 30                  35                  40

ATT CCA CAG AAT TTC ATA GCT GAC TAC TTT GAG ACG AGC AGC CAG TGC   254
Ile Pro Gln Asn Phe Ile Ala Asp Tyr Phe Glu Thr Ser Ser Gln Cys
             45                  50                  55

TCC AAG CCG GGT GTC ATC TTC CTA ACC AAG CGA AGC CGG CAG GTC TGT   302
Ser Lys Pro Gly Val Ile Phe Leu Thr Lys Arg Ser Arg Gln Val Cys
         60                  65                  70

GCT GAC CCC AGT GAG GAG TGG GTC CAG AAA TAT GTC AGC GAC CTA GAG   350
Ala Asp Pro Ser Glu Glu Trp Val Gln Lys Tyr Val Ser Asp Leu Glu
     75                  80                  85

CTG AGT GCC TGAGGGGTCC AGAAGCTTCG AGGCCCAGCG ACCTCGGTGG           399
Leu Ser Ala
 90

GCCAGTGGGG AGGAGCAGGA GCCTGAGCCT TGGGAAACAT GCGTGTGACC TCCACAGCTA 459

CCTCTTCTAT GGACTGGTTG TTGCCAAACA GCCACACTGR GGGACTCTTC TTAACTTAAA 519

TTTTAATTTA TTTATTTATA CTATTTAGTT TTTGTAATTT ATTTTCGATT TCACAGTGTG 579

TTTGTGATTG TTTGCTCTGA GAGTTCCCCT GTCCCCTCCC CCTTCCCTCA CACCGCGTCT 639
```

| | | | | | | | | |
|---|---|---|---|---|---|---|---|---|
| GGTGACAACC | GAGTGGCTGT | CATCAGCCTG | TGTAGGCAGT | CATGGCACCA | AAGCCACCAG | 699 |
| ACTGACAAAT | GTGTATCGGA | TGCTTTTGTT | CAGGGCTGTG | ATCGGCCTGG | GGAAATAATA | 759 |
| AAGAACGCTC | TTTTAAAAGG | TAAAAAAAAA | AAAAAAAAA A | | 800 |

( 2 ) INFORMATION FOR SEQ ID NO:2:

( i ) SEQUENCE CHARACTERISTICS:
        ( A ) LENGTH: 92 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Gln Val Ser Thr Ala Ala Leu Ala Val Leu Leu Cys Thr Met Ala
 1               5                  10                  15

Leu Cys Asn Gln Phe Ser Ala Ser Leu Ala Ala Asp Thr Pro Thr Ala
                 20                  25                  30

Cys Cys Phe Ser Tyr Thr Ser Arg Gln Ile Pro Gln Asn Phe Ile Ala
             35                  40                  45

Asp Tyr Phe Glu Thr Ser Ser Gln Cys Ser Lys Pro Gly Val Ile Phe
         50                  55                  60

Leu Thr Lys Arg Ser Arg Gln Val Cys Ala Asp Pro Ser Glu Glu Trp
 65                  70                  75                  80

Val Gln Lys Tyr Val Ser Asp Leu Glu Leu Ser Ala
                 85                  90
```

( 2 ) INFORMATION FOR SEQ ID NO:3:

( i ) SEQUENCE CHARACTERISTICS:
        ( A ) LENGTH: 737 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens
        ( G ) CELL TYPE: T-cell
        ( H ) CELL LINE: C10-MJ2

( i x ) FEATURE:
        ( A ) NAME/KEY: CDS
        ( B ) LOCATION: 34..315

( x i ) SEQUENCE DESCRIPTION: SEQ ID NO:3:

```
CTCGAGCCCA CATTCCATCA CCTGCTCCCA ATC ATG CAG GTC TCC ACT GCT GCC   54
                                    Met Gln Val Ser Thr Ala Ala
                                     1               5

CTT GCC GTC CTC CTC TGC ACC ATG GCT CTC TGC AAC CAG GTC CTC TCT  102
Leu Ala Val Leu Leu Cys Thr Met Ala Leu Cys Asn Gln Val Leu Ser
         10                  15                  20

GCA CCA CTT GCT GCT GAC ACG CCG ACC GCC TGC TGC TTC AGC TAC ACC  150
Ala Pro Leu Ala Ala Asp Thr Pro Thr Ala Cys Cys Phe Ser Tyr Thr
             25                  30                  35

TCC CGA CAG ATT CCA CAG AAT TTC ATA GCT GAC TAC TTT GAG ACG AGC  198
Ser Arg Gln Ile Pro Gln Asn Phe Ile Ala Asp Tyr Phe Glu Thr Ser
 40                  45                  50                  55

AGC CAG TGC TCC AAG CCC AGT GTC ATC TTC CTA ACC AAG AGA GGC CGG  246
Ser Gln Cys Ser Lys Pro Ser Val Ile Phe Leu Thr Lys Arg Gly Arg
                 60                  65                  70

CAG GTC TGT GCT GAC CCC AGT GAG GAG TGG GTC CAG AAA TAC GTC AGT  294
Gln Val Cys Ala Asp Pro Ser Glu Glu Trp Val Gln Lys Tyr Val Ser
```

-continued

```
                     75                        80                         85
GAC CTG GAG CTG AGT GCC TGAGGGGTCC AGAAGCTTCG AGGCCCAGCG                         342
Asp Leu Glu Leu Ser Ala
        90

ACCTCGGTGG GCCAGTGGGG AGGAGCAGGA GCCTGAGCCT TGGGAAACAT GCGTGTGACC               402

TCCACAGCTA CCTCTTCTAT GGACTGGTTG TTGCCAAACA GCCACACTGR GGGACTCTTC               462

TTAACTTAAA TTTTAATTTA TTTATTTATA CTATTTAGTT TTTGTAATTT ATTTTCGATT               522

TCACAGTGTG TTTGTGATTG TTTGCTCTGA GAGTTCCCCT GTCCCCTCCC CCTTCCCTCA               582

CACCGCGTCT GGTGACAACC GAGTGGCTGT CATCGGCCTG TGTAGGCAGT CATGGCACCA               642

AAGCCACCAG ACTGACAAAT GTGTATCAGA TGCTTTTGTT CAGGGCTGTG ATCGGCCTGG               702

GGAAATAATA AAGATGTTCT TTTAAACGGT AAAAA                                          737
```

( 2 ) INFORMATION FOR SEQ ID NO:4:

( i ) SEQUENCE CHARACTERISTICS:
        ( A ) LENGTH: 93 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Gln Val Ser Thr Ala Ala Leu Ala Val Leu Leu Cys Thr Met Ala
 1            5                  10                 15

Leu Cys Asn Gln Val Leu Ser Ala Pro Leu Ala Ala Asp Thr Pro Thr
             20                 25                 30

Ala Cys Cys Phe Ser Tyr Thr Ser Arg Gln Ile Pro Gln Asn Phe Ile
         35                 40                 45

Ala Asp Tyr Phe Glu Thr Ser Ser Gln Cys Ser Lys Pro Ser Val Ile
     50                 55                 60

Phe Leu Thr Lys Arg Gly Arg Gln Val Cys Ala Asp Pro Ser Glu Glu
 65                 70                 75                 80

Trp Val Gln Lys Tyr Val Ser Asp Leu Glu Leu Ser Ala
                 85                 90
```